United States Patent [19]
Thames et al.

[11] Patent Number: 5,807,922
[45] Date of Patent: Sep. 15, 1998

[54] MULTIFUNCTIONAL SURFACE ACTIVE AGENTS, SYNTHESES AND APPLICATIONS THEREOF

[75] Inventors: Shelby Freland Thames; Kamlesh Gopichand Panjnani, both of Hattiesburg, Miss.; Rajan Hariharan, Norcross, Ga.

[73] Assignee: University of Southern Mississippi, Hattiesburg, Miss.

[21] Appl. No.: 739,850

[22] Filed: Oct. 30, 1996

[51] Int. Cl.$^6$ ........................................... C08K 5/16
[52] U.S. Cl. .................... 524/725; 524/730; 524/728; 524/714; 528/26; 528/28; 528/31; 556/438; 556/417; 556/419; 556/423; 556/413
[58] Field of Search .................. 556/438, 417, 556/419, 423, 413; 524/730, 725, 728, 714; 528/26, 28, 31

[56] References Cited

U.S. PATENT DOCUMENTS

| | | | |
|---|---|---|---|
| 3,879,433 | 4/1975 | Omietanski et al. | 260/448.2 |
| 4,150,048 | 4/1979 | Schilling, Jr. et al. | 260/448.2 |
| 4,176,127 | 11/1979 | Hempel et al. | 260/407 |
| 4,512,926 | 4/1985 | Kampf et al. | 260/398 |
| 4,520,160 | 5/1985 | Brown | 556/445 |
| 5,124,469 | 6/1992 | Takago et al. | 556/438 |
| 5,180,771 | 1/1993 | Arai et al. | 524/588 |
| 5,247,044 | 9/1993 | Crivello et al. | 528/15 |
| 5,508,459 | 4/1996 | Arai et al. | 556/438 |

FOREIGN PATENT DOCUMENTS

| | | | |
|---|---|---|---|
| 0 314 903 A3 | 5/1989 | European Pat. Off. | C08G 77/46 |
| 0 378 370 A2 | 7/1990 | European Pat. Off. | C08J 3/16 |
| 0 459 705 A2 | 12/1991 | European Pat. Off. | C08G 77/46 |
| 0 520 392 A1 | 12/1992 | European Pat. Off. | C08J 9/00 |
| 0 585 044 A2 | 3/1994 | European Pat. Off. | C08G 77/46 |
| 0 659 837 A2 | 6/1995 | European Pat. Off. | C08J 83/12 |
| 282 014 A5 | 8/1990 | German Dem. Rep. | C07F 7/08 |
| 282 692 A5 | 9/1990 | German Dem. Rep. | C07F 7/08 |
| 2 218 097 | 11/1989 | United Kingdom . | |

*Primary Examiner*—Margaret W. Glass
*Attorney, Agent, or Firm*—Balaram Gupta

[57] ABSTRACT

Novel organosilane derivatized long-chain compounds containing halosilane and hydroxysilane groups are disclosed and claimed. A process for the syntheses of these novel compositions is also disclosed, which involves simple one-pot hydrosilylation reaction of substituted halosilanes with substituted long-chain olefinic compounds, and subsequent hydrolysis to form surface active silanol derivatives. Preferred embodiments include organosilane derivatives of fatty acids derived from tung oil, high erucic acid rape seed oil, and linseed oil. These compositions feature high surface activity in forming stable organic/water emulsions of various difficultly emulsifiable materials as compared with conventional emulsifying agents. These compositions are useful as reactive-dispersants, defoamers, reactive-surfactants in emulsion polymerization, crosslinkers, film formers, gloss enhancers, anticorrosive additives, adhesion promoters and as general property enhancers in coatings, adhesives and inks. These compositions contribute zero volatile organic components (VOC) to these formulations.

8 Claims, No Drawings

MULTIFUNCTIONAL SURFACE ACTIVE AGENTS, SYNTHESES AND APPLICATIONS THEREOF

BACKGROUND OF THE INVENTION

1. Field of the Invention

This invention relates to a novel composition of organosilane derivatized long-chain olefinic compounds prepared by the hydrosilylation reaction of a substituted halosilane and a substituted long-chain olefinic compound. More particularly, though not exclusively, this invention relates both to novel compositions of organosilane derivatized fatty compounds and to processes for making those compositions. The invention is also directed to organosilanol derivatized long-chain olefinic compounds that are surface active agents having utility in coatings, adhesives and inks to improve and enhance the general application properties of these formulations.

2. Description of the Prior Art

A wide variety of additives used in such formulations as in coatings, inks, and adhesives contain volatile organic compounds (VOCs). A major utility of these additives includes as surface active agents, i.e., as surfactants, dispersants, corrosion inhibitors, and as defoamers. However, the VOCs in these formulations are released to the atmosphere during their use and cause undesirable side effects. As a result, Congress has passed Clean Air Act of 1990 forcing the coating manufacturers to develop low to no VOC formulations. Although water based formulations for the above mentioned applications are being developed, there is still a need for more cost effective multi-functional surface active agents that are suitable for forming stable emulsions of these formulations.

One approach that is used in the prior art which is relevant to this invention is hydrosilylation of a variety of compounds to form surface active agents. Hydrosilylation involves a reaction of a Si—H containing compound with an olefinic compound to form a organosilane compound. A number of so formed organosilane compounds feature surface active properties. Examples of such compositions are described in Eur. Pat. Appl. No. 659,837; Eur. Pat. Appl. No. 585,044; and U.S. Pat. No. 5,247,044; which are hereby incorporated herein by reference in their entirety.

There are also extensive literature references on surfactant compositions based on siloxane-polyether compositions particularly useful in polyurethane foam applications and for forming stable emulsions. Specific examples of such surfactant compositions are described in Eur. Pat. Appl. No. 520,392; Eur. Pat. Appl. No. 459,705; East German DD 282,692 and 282,014; Eur. Pat. Appl. No. 378,370; German patent DE 3,913,485; and Eur. Pat. Appl. No. 314,903; which are hereby incorporated herein by reference in their entirety.

A few references also disclose synthesis of organopolysiloxanes by a hydrosilylation reaction using a platinum catalyst. Examples of such hydrosilylation reactions are described in U.S. Pat. No. 4,520,160; U.S. Pat. No. 4,150,048; and Ger. Offen. DE 2,364,887; which are hereby incorporated herein by reference in their entirety.

A major drawback of these references is that they all involve the reaction of complicated polymeric siloxanes, which are either expensive and are not readily available. In addition, none of the references discussed above utilizes simple, cost effective, and readily available monomeric Si—H containing compounds. Furthermore, none of the references mentioned above teaches a simple hydrosilylation reaction involving a cheap, readily available halosilane with a long-chain olefinic compound, and subsequently hydrolyzing these products in an aqueous phase to form instantly the surface active agents. Most importantly, none of the references mentioned above discloses preparation of stable organosilanol compounds having excellent surfactant properties.

Therefore, it is an object of this invention to provide novel compositions derived from simple halosilanes containing Si—H bonds by the reaction of the halosilanes with a wide variety of long-chain olefinic compounds. An additional objective of this invention is to provide hitherto unknown novel organosilanediol and organosilanol compositions, which spontaneously emulsify and form stable emulsions by a simple aqueous hydrolysis of the novel halosilane compositions. Yet another objective of this invention is to provide a process for the preparation of the novel halosilane and silanol compositions. It is also an objective of this invention to provide a variety of utilities for these novel compositions. Such utilities include applications as dispersants, defoamers, gloss enhancers, crosslinkers, surfactants, adhesion promoters, and as anti-corrosive additives thus enhancing the general application and performance properties of paints, coatings, adhesives and inks yet contributing zero VOCs to these formulations. The compositions of the present invention have no precedence in the prior art.

Prior Art

The following references are disclosed as background prior art.

U.S. Pat. No. 4,150,048 discloses a process for making novel compositions of nonhydrolyzable siloxane block copolymers of organosiloxanes and organic ethers by the reaction of organic ethers having olefinic end groups with organohydrosiloxanes.

U.S. Pat. No. 4,520,160 discloses a method for making organopolysiloxane emulsifier compositions by a hydrosilylation reaction.

U.S. Pat. No. 5,247,044 teaches a synthesis of silicon polyether copolymers from ring opening polymerization of epoxides in the presence of Si—H containing compounds.

Eur. Pat. Appln. No. 314,903 discloses a process for the preparation of siloxane-oxyalkylene copolymers by a solventless process via hydrosilylation of oxyethylene rich polyethers.

Eur. Pat. Appln. No. 378,370 describes a process for making silicon-containing polymer particles useful for preparing uniform, crosslinked silicone rubber particles.

Eur. Pat. Appln. No. 459,705 discloses a novel surface active organopolysiloxane compositions obtained by hydrosilylation procedure for forming water-in-oil emulsions for emulsifying oils.

Eur. Pat. Appln. No. 520,392 teaches an improved surfactant composition for flexible polyurethane foam.

Eur. Pat. Appln. No. 585,044 discloses a novel polysiloxane polyether useful as a silicone surface active agent.

Eur. Pat. Appln. No. 659,837 describes an improved process for the preparation of siloxane-oxyalkylene block copolymer utilizing hydrosilylation reaction with a phenyl ether.

Ger. Offen. DE 2,364,887 discloses hydroxyalkyl siloxanes as foam stabilizers.

German patent DE 3,913,485 discloses surface-active N-(silylpropyl)- perfluoroalkanesulfonamides which were prepared by condensation and hydrosilylation procedure.

Ger. (East) DD 282,692 and 282,014 disclose siloxanylalkenol useful as surfactants synthesized by hydrosilylation procedure.

*J. Fluorine Chem.,* (1991), Vol. 55(1), (pp 79–83) describes a synthesis of new silanes derived from non-ionic F-alkylated surfactants by hydrosilylation procedure.

*Appl. Organomet. Chem.,* (1992), Vol. 6(8), (pp 701–8) discloses novel nonionic siloxane surfactants which were obtained by the hydrosilylation of butynediol-oligo (oxyethylenes) with polysiloxanes.

*Second International Symposium on Film Formation,* Chicago, Ill. (1995) discusses about the Clean Air Act of 1990.

*Polymeric Materials Science and Engineering,* (1995), Vol. 73, (pp 366) also discusses about the Clean Air Act of 1990.

All of the references described herein are incorporated herein by reference in their entirety.

SUMMARY OF THE INVENTION

Surprisingly, it has now been found that an organosilane derivatized long-chain olefinic compound can be readily formed by a simple one-step reaction of a long-chain olefinic compound with a Si—H containing moiety. The organosilane derivatives so formed are highly surface active and spontaneously hydrolyze when contacted with water to form stable emulsions which have excellent surfactant properties. This invention thus provides hitherto unknown, stable, novel organosilanediol and organosilanol compositions, with properties unattainable by prior art approaches. This invention also provides novel processes whereby such novel compositions of matter are prepared with inherent capability to form stable emulsions. Preferred long-chain olefinic compounds of this invention are olefinic fatty acid esters or oils.

More particularly, the organosilane derivatized compounds of the present invention are derived from a long-chain olefinic compound of the formula:

wherein R has the formula:

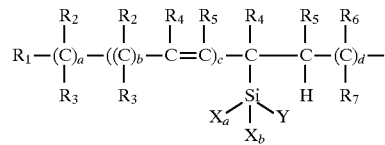

wherein (a) $R_1,R_2,R_3,R_4,R_5,R_6$, and $R_7$ are the same or different and are each independently selected from the group consisting of hydrogen, alkoxy group having 1 to 10 carbon atoms, phenyl and substituted phenyl, tolyl and substituted tolyl, alkyl and fluoroalkyl groups having the formula $C_nH_xF_y$, where n is an integer from 1 to 10, x and y are integers from 0 to 2n+1, and the sum of x and y is 2n+1; (b) $R_8$ is selected from the group consisting of —COOR', —CN, —CONR"R''',—CH$_2$NR"R''', and suitable salts thereof, where R', R", and R''' are the same or different and are independently selected from the group consisting of phenyl and substituted phenyl, tolyl and substituted tolyl, benzyl and substituted benzyl, a linear or branched alkenyl group having 2 to 10 carbon atoms, a linear or branched alkyl and fluoroalkyl group having the formula $C_nH_xF_y$, where n is an integer from 1 to 10, x and y are integers from 0 to 2n+1, and the sum of x and y is 2n+1, and R' can also be a multifunctional moiety having the structure:

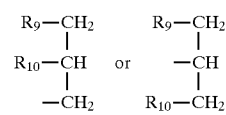

where $R_9$ and $R_{10}$ are the same and may be the same as carboxylated R or different and are independently selected from the group consisting of a substituted or unsubstituted, saturated or unsaturated fatty acid chain, acrylic and substituted acrylic, and a linear or branched alkyl and alkenyl carboxylic acid moiety having 2 to 20 carbon atoms; (c) $X_a$ and $X_b$ are the same or different and are selected from the group consisting of Br, Cl, I, hydroxy, alkoxy group having 1 to 10 carbon atoms, a mixed polyalkyleneoxy group having 2 to 4 carbon atoms, polyethyleneoxy, polypropyleneoxy, phenoxy, benzoxy, and substituted polyaryloxy group having 7 to 20 carbon atoms; (d) Y is same as $X_a$ or $X_b$, or an aliphatic or an aromatic moiety having 1 to 20 carbon atoms; and (e) a, b, c, and d are integers, where a ranges from about 0 to about 20, b ranges from about 0 to about 4, c ranges from about 0 to about 4, and d ranges from about 0 to about 20.

This invention is also based in part on the use of the organosilanol derivatized long-chain olefinic compounds as surfactants or defoamers in the preparation of paint formulations for a variety of coating applications. The emulsions formed from the organosilanol derivatized long-chain olefinic compounds can be used in water systems as wetting agents, and emulsifiers. They are particularly suitable for dispersing pigments or anti-corrosive additive materials in paints or inks. These materials are also suitable as surfactants in emulsion polymerization.

DETAILED DESCRIPTION OF THE INVENTION

Surprisingly, it has now been found that an organosilane derivatized long-chain olefinic compound can be readily formed by a simple one-step reaction of a long-chain olefinic compound with a Si—H containing moiety. The organosilane derivatives so formed are highly surface active and spontaneously hydrolyze when contacted with water to form stable emulsions which have excellent surfactant properties. This invention thus provides hitherto unknown, stable, novel organosilanediol and organosilanol compositions, with properties unattainable by prior art approaches. This invention also provides novel processes whereby such novel compositions of matter are prepared with inherent capability to form stable emulsions. Preferred long-chain olefinic compounds of this invention are olefinic fatty acid esters or oils.

More particularly, the organosilane derivatized compounds of the present invention are derived from a long-chain olefinic compound of the formula:

wherein R has the formula:

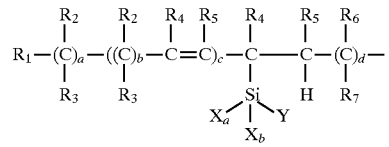

wherein (a) $R_1,R_2,R_3,R_4,R_5,R_6$, and $R_7$ are the same or different and are each independently selected from the group consisting of hydrogen, alkoxy group having 1 to 10 carbon atoms, phenyl and substituted phenyl, tolyl and substituted tolyl, alkyl and fluoroalkyl group having the formula $C_nH_xF_y$, where n is an integer from 1 to 10, x and y are integers from 0 to 2n+1, and the sum of x and y is 2n+1; (b) $R_8$ is selected from the group consisting of —COOR', —CN, —CONR''R''', —CH$_2$NR''R''', and suitable salts thereof, where R', R'', and R''' are the same or different and are independently selected from the group consisting of phenyl and substituted phenyl, tolyl and substituted tolyl, benzyl and substituted benzyl, a linear or branched alkenyl group having 2 to 10 carbon atoms, a linear or branched alkyl and fluoroalkyl group having the formula $C_nH_xF_y$, where n is an integer from 1 to 10, x and y are integers from 0 to 2n+1, and the sum of x and y is 2n+1, and R' can also be a multifunctional moiety having the structure:

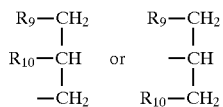

where $R_9$ and $R_{10}$ are the same and may be the same as carboxylated R or different and are independently selected from the group consisting of a substituted or unsubstituted, saturated or unsaturated fatty acid chain, acrylic and substituted acrylic, and a linear or branched alkyl and alkenyl carboxylic acid moiety having 2 to 20 carbon atoms; (c) $X_a$ and $X_b$ are the same or different and are selected from the group consisting of Br, Cl, I, hydroxy, alkoxy group having 1 to 10 carbon atoms, a mixed polyalkyleneoxy group having 2 to 4 carbon atoms, polyethyleneoxy, polypropyleneoxy, phenoxy, benzoxy, and substituted polyaryloxy group having 7 to 20 carbon atoms; (d) Y is same as $X_a$ $X_b$, or an aliphatic or an aromatic moiety having 1 to 20 carbon atoms; and (e) a, b, c, and d are integers, where a ranges from about 0 to about 20, b ranges from about 0 to about 4, c ranges from about 0 to about 4, and d ranges from about 0 to about 20.

The long-chain olefinic compounds are preferably linear long-chain olefinic esters wherein $R_8$ is —COOR' and are unsubstituted. Accordingly, $R_1,R_2,R_3,R_4,R_5,R_6$, and $R_7$ in the above structure are hydrogen. In one of the preferred embodiments, the R' group in this structure is a multifunctional moiety having the structure:

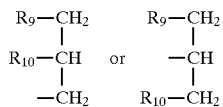

where $R_9$ and $R_{10}$ are as defined above. More preferably, $R_9$ and $R_{10}$ are same as the carboxylated long-chain olefinic group R or may be different and are independently selected from the group consisting of a substituted or unsubstituted saturated or unsaturated fatty acid chain.

The preferred long-chain olefinic esters are fatty oils. A variety of fatty oils having at least one olefinic bond in their fatty ester chain are suitable to form the organosilane derivative of the present invention. Representative examples of such fatty oils are cotton seed oil, sunflower oil, safflower oil, soybean oil, linseed oil, perilla oil, tung oil, Chinese melon oil, oiticica oil, rape seed oil, high erucic acid rape seed oil, crambe oil, vernonia oil, hemp oil, poppy seed oil, and cod-liver oil. The hydroxy fatty acids containing oils such as castor oil or lesquerella oil may also be employed provided that the hydroxy group is suitably protected. Thus, for example, dehydrated castor oil and/or modified or derivatized castor oil are particularly suitable for forming organosilane derivative of the present invention.

A wide variety of long-chain olefinic acids are suitable for the formation of organosilane derivatives of the present invention. Typical examples of such long-chain olefinic acids are eleostearic acid, oleic acid, elaidic acid, linoleic acid, linolenic acid, erucic acid, brassidic acid, nervonic acid, arachidonic acid, and undecylenic acid. In addition, as mentioned above in one of the preferred embodiments, the R' group is a multifunctional moiety of the structure described above. This multifunctional moiety is derived from a glycerol molecule often called triglycerides and most commonly present in all of the naturally occurring fatty esters including vegetable and animal derived fatty esters (i.e., triglycerides).

Preferred $R_9$ and $R_{10}$ groups in this multifunctional moiety could be either saturated or unsaturated long-chain acid groups and are derived from either naturally occurring fatty esters (i.e., triglycerides) or synthetic long-chain carboxylic acids. Illustrative examples of saturated long-chain carboxylic acids are n-hexanoic acid, n-heptanoic acid, octanoic acid, nonanoic acid, decanoic acid, lauric acid, myristic acid, palmitic acid, margaric acid, stearic acid, arachidic acid, behenic acid, lignoceric acid, cerotic acid, melissic acid and the like. Similarly, illustrative examples of unsaturated carboxylic acids are acrylic acid, methacrylic acid, cinnamic acid, crotonic acid, isocrotonic acid, angelic acid, tiglic acid, eleostearic acid, oleic acid, elaidic acid, linoleic acid, linolenic acid, erucic acid, brassidic acid, nervonic acid, arachidonic acid, undecylenic acid, and the like. Various saturated and unsaturated dicarboxylic acids may also be used provided that one of the carboxylic groups in these acids is suitably protected. Illustrative examples of such dicarboxylic acids include maleic acid, fumaric acid, and the like.

In one of the preferred embodiments, the long-chain olefinic ester is derived from a fatty oil selected from the group consisting of tung oil, high erucic acid rape seed oil, and linseed oil. In this embodiment, the $X_a$ and $X_b$ groups on the silicon atom may be the same or different and are preferably selected from the group consisting of Cl, Br, I, hydroxy, an alkoxy group having 1 to 20 carbon atoms, a mixed polyalkyleneoxy group having 2 to 4 carbon atoms, polyethyleneoxy group of the formula CH$_3$O(CH$_2$—CH$_2$O)$_n$—, and polypropyleneoxy group of the formula CH$_3$O (CH$_2$—CH(CH$_3$)O)$_n$—, where n is an integer ranging from about 10 to about 250. The mixed polyalkyleneoxy groups may be formed from a mixture of glycols such as ethylene glycol, propylene glycol, 1,2-butylene glycol, and the like. The mixed glycol linkages may be in a random order or in blocks of one kind. An example of a mixed polyalkyleneoxy group includes polyethyleneoxy-propyleneoxy group of the formula, CH$_3$O(CH$_2$—CH$_2$O)$_a$—(CH$_2$—CH(CH$_3$)O)$_b$—, where a and b are integers ranging from about 10 to about 250.

The Y group on the silicon atom is either an alkyl group having 1 to 4 carbon atoms or a polyethyleneoxy or a polypropyleneoxy group as described above. Most preferably, $X_a$ and $X_b$ groups are either chlorine, polyethyleneoxy, polypropyleneoxy, or a hydroxy group; and Y is an alkyl group having 1 to 4 carbon atoms such as methyl, ethyl, propyl or butyl group, or an aryl group such as phenyl or benzyl group, or a polyethyleneoxy group of a suitable molecular weight. The substituents $X_a$, $X_b$, and Y on silicon atom are selected in such a way that the hydrophilic/lipophilic balance (HLB) number of the resulting organosilane derivatized fatty ester is preferably in the range of from about 10 to about 18.

The HLB number referred to hereinabove is an empirical measure of the relative strengths of the hydrophilic and lipophilic parts of a surfactant molecule. Generally, the HLB number of a compound is calculated by the following equation:

$$HLB = \frac{\text{Percent hydrophilic character}}{5}$$

where percent hydrophilic character of a molecule may be calculated as follows:

$$\text{Percent hydrophilic character} = \frac{\text{Molecular Weight of the hydrophilic group in a compound}}{\text{Molecular weight of the compound}} \times 100$$

Thus, the HLB number scale runs from 0 to 20 in arbitrary units, wherein 0 represents a surfactant overwhelmingly lipophilic in character; and 20 a surfactant overwhelmingly hydrophilic in character. A description of HLB numbers may be found in "Paint Flow and Pigment Dispersion," T. C. Patton, (1964, John Wiley), pp 247–251, incorporated herein by reference in its entirety.

Therefore, it is possible to vary the HLB numbers by incorporating either polyethyleneoxy or polypropyleneoxy groups of varying molecular weights into the organosilane derivatized fatty esters of the present invention. This is particularly important because surfactants of varied HLB numbers can now be synthesized for different dispersant or surfactant applications.

The present invention also provides a novel, unique, and efficient process for preparing novel organosilane derivatized long-chain olefinic compounds of the present invention, which can be readily converted into compositions such as stable emulsions by simple hydrolysis techniques. Accordingly, the process comprises the steps of (a) subjecting a substituted long-chain olefinic compound to suitable hydrosilylation conditions in the presence of a Si—H containing moiety having at least one halogen substituent and a suitable catalyst for a sufficient period of time and under suitable conditions of temperature and pressure to form the corresponding hydrosilylated long-chain compound; and (b) subjecting said hydrosilylated compound to suitable hydrolysis conditions for a sufficient period of time and under suitable conditions of temperature and pressure to form the composition containing the organosilanol derivatized long-chain compound.

The starting material, i.e., the substituted long-chain olefinic compound has the formula:

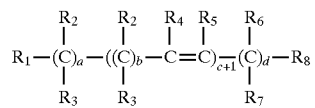
(I)

wherein $R_1, R_2, R_3, R_4, R_5, R_6, R_7 R_8$, a, b, c and d are as defined above. Preferably, the long-chain olefinic compound is a long-chain olefinic ester derived from a fatty oil selected from the group consisting of cotton seed oil, sunflower oil, safflower oil, soybean oil, linseed oil, perilla oil, tung oil, Chinese melon oil, oiticica oil, rape seed oil, high erucic acid rape seed oil, crambe oil, vernonia oil, modified or dehydrated castor oil, modified or dehydrated lesquerella oil, hemp oil, poppy seed oil, and cod-liver oil. As stated earlier, the oils containing the hydroxy fatty acid moieties may also be used as starting materials provided that the hydroxy group is suitably protected.

The long-chain olefinic ester may also be an olefinic ester derived from a fatty oil and preferably selected from the group consisting of eleostearic acid, oleic acid, elaidic acid, linoleic acid, linolenic acid, erucic acid, brassidic acid, nervonic acid, arachidonic acid, and undecylenic acid. Most preferably, the long-chain olefinic ester is selected from the group consisting of high erucic acid rape seed oil, linseed oil, tung oil, and methyl ester of eleostearic acid.

Utilizing the substituted long-chain olefinic compound (Formula I), it is believed that the process proceeds as shown in Scheme I below:

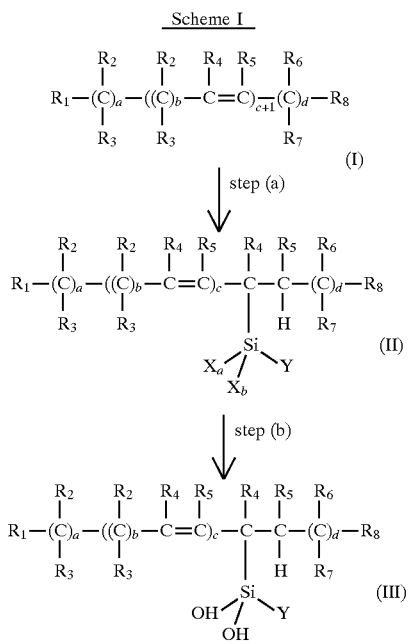

The hydrosilylation of the olefinic compound can be carried out by reacting it with a wide variety of Si—H containing moieties. The Si—H containing moiety is typically an organosilane molecule having a general formula $X_aX_bYSi$—H, where $X_a, X_b$, and Y are the same or different and are as defined above. Illustrative examples of such organosilane molecules are trichlorosilane, dichloromethylsilane, dibromomethylsilane, diiodomethylsilane, dichloroethylsilane, dichlorophenylsilane, dichlorobutylsilane, dichloromethoxysilane, chloro-methoxy-methylsilane, and the like. Preferably, the silane is a dichloroalkylsilane, where alkyl group contains 1 to 4 carbon atoms. The most preferred organosilane is dichloromethylsilane.

The hydrosilylation reaction is generally carried out by mixing the olefinic compound with a suitable organosilane compound as described above in the presence of a suitable catalyst. Optionally, a solvent may be employed for this reaction. Any solvent, polar or nonpolar aprotic with relatively high vapor pressure, that solubilizes the olefinic compound may be employed. Suitable solvents include toluene, hexane, cyclohexane, petroleum ether, methylene chloride, chloroform, acetonitrile, ethyl acetate, sulfolane, and the like. The solvent is generally not required when the olefinic compound is of low viscosity such as methyl ester of eleostearic acid.

Various catalysts that are effective for hydrosilylation reaction may be employed. Typically, catalysts derived from Group VIII transition metals are used for hydrosilylation reactions. Suitable Group VIII metal-containing catalysts are well known and include platinum-, palladium-, and rhodium-containing catalysts. Catalysts such as platinum on a carrier, for example, alumina or charcoal, finely divided platinum, and chloroplatinic acid are also suitable for carrying out hydrosilylation. Various other catalysts may also be employed for affecting the hydrosilylation reaction, which include nucleophilic (e.g., bases such as amines, phosphines, etc.), electrophilic (e.g., $ZnCl_2CuCl_2$, etc.), and other metal catalysts. A detailed description of the hydrosilylation catalysts may be found in "Comprehensive Handbook on Hydrosilylation," Ed. by B. Marciniec, (1992, Pergamon), pp 8–94, incorporated herein by reference in its entirety. Particularly useful and preferred catalyst is platinumdivinyltetramethyldisiloxane.

The amount of catalyst employed is any amount which would produce the desired end result. Generally, this amount would be in the range of from about 0.05 parts per million (ppm) to about 2000 ppm based on the starting long-chain olefinic compound.

The hydrosilylation reaction in step (a) can be carried out at suitable temperatures to affect the addition of Si—H bond to the olefinic bond of the long-chain olefinic compound. Typical reaction temperature ranges from about 25° C. to about 200° C. Preferably, the reaction is carried out at a temperature from about 40° C. to about 150° C. The pressure in this step (a) is not critical and can be sub-atmospheric, atmospheric or super-atmospheric.

The reaction times in step (a) will generally range from about 15 minutes to about 24 hours or longer and sometimes under an inert atmosphere such as nitrogen.

Using the procedure of step (a) outlined herein, the substituted long-chain olefinic compound undergoes hydrosilylation with Si—H containing moiety to form the corresponding organosilane derivatized long-chain olefinic compound of the Formula II in Scheme I, wherein $R_1,R_2,R_3,R_4,R_5,R_6,R_7,R_8,X_a,X_b$, Y, a, b, c, and d are as defined above.

The organosilane derivative as described hereinabove is hydrolyzed in step (b) to form compositions such as stable emulsions. The organosilane derivative undergoes spontaneous hydrolysis when contacted with water. The hydrolysis can be carried out under a variety of techniques well known in the art. Preferably, the hydrolysis is carried out in the presence of a suitable base when the organosilane derivative formed in step (a) contains a halogen substituent, i.e., when $X_a$ or $X_b$ is a halogen in the above structure.

The suitable base is any material which will function for the hydrolysis conditions and includes, without limitation, inorganic base such as a metal hydroxide, preferably an alkali metal hydroxide, an alkali metal carbonate, e.g., $K_2CO_3$; an alkali metal alkoxide (an ionic organic base), such as $NaOCH_3$, $KOC(CH_3)_3$, etc.; an alkali metal organic salt (an ionic organic base) such as potassium acetate, etc.; and an amine (a non-ionic organic base) such as pyridine, or a tri-lower-alkylamine, e.g., tripropylamine, trimethylamine, and triethylamine, etc. Ammonia can also be used as a base in step (b) of the present invention. The purpose of using the base in this step (b) is to neutralize the acid generated, for example, by the hydrolysis of Si—X. bond when $X_a$ is a halogen (which generates hydrohalic acid). If the hydrohalic acid so generated can be removed by some other means such as by an aspirator, then the amount of base needed can be significantly reduced.

Generally, the amount of base employed in step (b) is from about 0.1 moles to about 2 moles per mole of halogen present in the organosilane derivative formed in step (a). The preferred amount is from about 0.8 mole to about 1.2 mole per mole of halogen present in the organosilane derivative formed in step (a) if the hydrohalic acid generated cannot be removed by any other means as mentioned above.

The temperature at which hydrolysis in step (b) is conducted ranges from about 0° C. to about 100° C., preferably from about 10° C. to about 50° C. The pressure in this step (b) is not critical and can be sub-atmospheric, atmospheric or super-atmospheric.

The hydrolysis reaction in step (b) undergoes spontaneously if the organosilane derivative formed in step (a) contains a halogen substituent (i.e., $X_a$ or $X_b$=halogen), and therefore, the reaction times in step (b) will generally be shorter ranging from about 1 minute to about 2 hours.

Using the procedure of step (b) outlined herein, the organosilane derivatized long-chain compound formed in step (a) undergoes suitable hydrolysis to form the corresponding organosilanol derivatized long-chain compound of the Formula III in Scheme I, wherein $R_1,R_2, R_3,R_4,R_5,R_6, R_7,R_8$, Y, a, b, c, and d are as defined above.

Generally, the organosilanol derivatized long-chain compound (Formula III) forms a stable dispersion in an aqueous medium. The dispersion can readily be solubilized to form a clear solution using a wide variety of organic solvents. Examples of such solvents that can be used for solubilizing organosilanol derivative (Formula III) includes methanol, ethanol, t-butanol, acetone, methyl ethyl ketone, ethyl acetate, butyl acetate, and the like.

The organosilanol derivative (Formula III) can also be isolated as a colloidal dispersion, microemulsion, emulsion, or a suspension depending upon the type of the reactor used and depending upon the nature of the substituents, $X_a,X_b$, and Y used on the silicon atom. Generally, the nature of the dispersion formed depends upon the particle size of the organosilanol derivative (Formula III). Typically, the range of particle size in various compositions are as follows: solution—0.001 to 0.01 $\mu$m; colloidal dispersion (or solution)—0.001 to 0.1 $\mu$m; microemulsion—0.1 $\mu$m to 1.0 $\mu$m; emulsion—0.5 to 1.5 $\mu$m; and suspension—>1.0 $\mu$m. A detailed description of particle size in a dispersive composition may be found in "Water-Borne Coatings," (Hanser), pp 29–30, incorporated herein by reference in its entirety.

In another preferred embodiment of this invention, the organosilane compounds described herein and the method of preparing the same are useful in a wide diversity of applications. Particularly, the hydrolyzed organosilane compounds, i.e., the organosilanediol derivatives of the present invention are excellent emulsifying agents and form stable emulsions in water and thus are useful in a number of water-based formulations including paints, coatings, adhesives and inks formulations.

Various types of pigments, and anti-corrosive additives in paints, coatings and inks can be readily dispersed in the emulsions formed from the organosilanol derivatives of the present invention. The organosilanol derivatives of the present invention are obtained in the step (b) by the spontaneous hydrolysis of the organosilane derivatives formed in the step (a) of the process of the present invention. The organosilanol derivative so formed functions as a hydrosilylated surfactant and thus aids in the dispersion of a variety of pigments and anticorrosive additives.

The emulsions containing the organosilanol derivatives also impart a number of enhanced performance characteristics to the above mentioned formulations. The improved performances include, enhancement of gloss in paints, coatings and inks. The organosilanol derivatives also function as a defoamer in paints, coatings, inks, and adhesive formulations; as a crosslinker in paints, coatings, adhesives, and inks; as a corrosion inhibitor in paints; and as an adhesion promoter in paints, coatings, adhesives, and inks.

A further embodiment of the present invention is the use of the hydrosilylated surfactants of the present invention in emulsion polymer syntheses and subsequent use in coatings and adhesives including pressure sensitive and contact adhesives. These formulations can be used either at ambient conditions or at thermosetting conditions generally at elevated temperatures. The latex formulations formed in the emulsion polymerizations are also suitable to form inks.

Thus, a latex formulation containing the organosilanol derivatives of the present invention can be readily formed as follows. First, an emulsion containing the organosilanol derivatives in deionized water is formed. Then, a suitable monomer mixture to form the latex is fed into the emulsion in the presence of a suitable free radical initiator. The polymerization of the monomer mixture takes place in the resulting mixture to form a latex.

Various monomers may be employed for the formation of the latex. Examples of suitable monomers include, without limitation, vinyl acetate, methyl acrylate, butyl acrylate, methyl methacrylate, butyl methacrylate, phenyl acrylate, vinyl chloride, acrylonitrile, acrylamide, 2-ethylhexyl acrylate, 2-hydroxyethyl methacrylate, 2-hydroxyethyl acrylate, glycidyl acrylate, glycidyl methacrylate, vinyl ester of versatic acid and the like. Various free radical initiators well known in the art may be used for the polymerization of the monomers. Representative examples of free radical initiators include ammonium persulfate, sodium persulfate, and potassium persulfate.

Optionally, the latex compositions of the present invention may also contain one or more additives such as wet adhesion promoters, protective/stabilizing colloids, fillers, water-dispersible resins, coloring agents, antiseptics, biocides, and the like. Particularly important additive employed in the latex composition of the present invention is a wet adhesion promoter. The wet adhesion promoter improves the adhesion of a latex to various surfaces such as plastic, glass, wood, metal, composites, ceramics, and the like. Several adhesion promoters well known in the art may be used with the latex of the present invention. Illustrative examples of such adhesion promoters include Sipomer®, WAM I and WAM II, sold by Rhone-Poulenc. The wet adhesion promoters may be present in an amount ranging from about 0.5 weight percent to about 5 weight percent based on the total weight of the latex.

In another aspect of the present invention, a process for the formation of polyalkyleneoxysilane derivatized long-chain fatty compounds is also provided. In this embodiment, the process as described above involves an additional intermediate step to introduce polyalkoxy groups by a substitution reaction. Accordingly, utilizing the substituted long-chain olefinic compound, Formula I, it is believed that the process comprising the additional intermediate step proceeds as shown in Scheme II below:

Scheme II

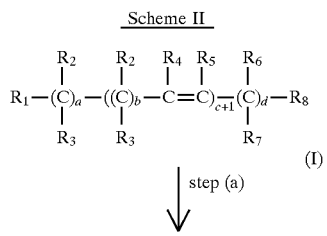

(I)

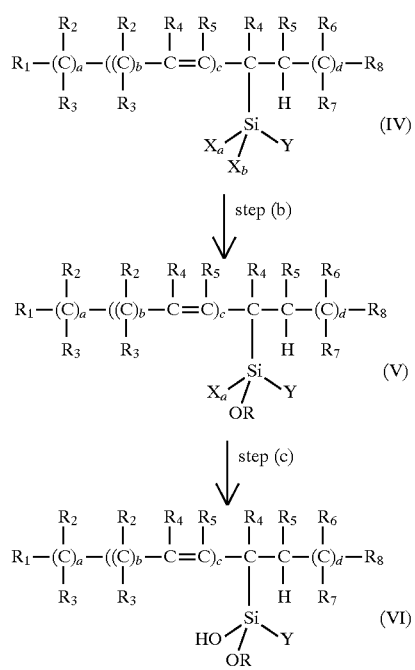

The starting material, i.e., the substituted long-chain olefinic compound, Formula I in Scheme II is the same starting material as described earlier in Scheme I, wherein $R_1, R_2, R_3, R_4, R_5, R_6, R_7, R_8$, a, b, c, and d are as defined above. Again, preferably the long-chain olefinic compound is a long-chain olefinic ester derived from a fatty oil as described above. The step (a), i.e., the hydrosilylation reaction described in Scheme II is identical to step (a) described in Scheme I, and can be carried out essentially under similar conditions as mentioned above. The substituents $X_a$, $X_b$ and Y on silicon in Formula IV are the same or different and are as defined above with the proviso that at least two of these substituents are halogens selected from the group consisting of Cl, Br, and I. Preferably, $X_a$ and $X_b$ are either Cl or Br, and Y is either Cl, Br, or an alkyl or an alkoxy group having 1 to 20 carbon atoms.

Accordingly, the hydrosilylation is carried out preferably in the presence of a dihalosilane compound in this process of the present invention. Representative examples of such dihalosilane, i.e., Si—H containing moieties include trichlorosilane, dichloromethylsilane, dibromomethylsilane, chlorobromomethylsilane, iodochloro-methylsilane, diiodomethylsilane, dichloroethylsilane, dichlorophenylsilane, dichlorobutylsilane, and dichloromethoxysilane.

The substitution step, i.e., step (b) in Scheme II involves a substitution reaction of organosilane derivatized long-chain compound, Formula IV with a polyalkyleneoxy compound. The step (b) in Scheme II can be carried out under a variety of techniques well known in the art. Preferably, the substitution step, step (b) in Scheme II can be carried out by adding the polyalkyleneoxy compound to the organosilane derivatized long-chain compound (Formula IV) under suitable conditions, optionally, in the presence of a solvent.

The amount of polyalkyleneoxy compound employed in the substitution step (step (b), Scheme II) depends upon the number of halogen atoms present in Formula IV. Typically, polyalkyleneoxy compound in the amounts of from about 0.1 to about 1.1 moles per mole of halogen in Formula IV is employed. Preferably, 0.5 mole of polyalkyleneoxy compound per mole of halogen in Formula IV is employed.

A wide variety of polyalkyleneoxy compounds of varied molecular weights can be used in the substitution step (step (b), Scheme II). Illustrative examples of such polyalkyleneoxy compounds include monomethyl capped polyethylene glycols (MPEG) of the formula, $CH_3O(CH_2—CH_2O)_n$ $CH_2—CH_2OH$; and monomethyl capped polypropylene glycols (MPPG) of the formula, $CH_3O(CH_2—CH(CH_3)O)_n$ $CH_2—CH(CH_3)OH$; where n is an integer ranging from about 10 to about 250. As stated earlier, a variety of mixed polyalkyleneoxy compounds having 2 to 4 carbon atoms may also be employed. Examples of such mixed polyalkyleneoxy compounds include monomethyl capped polyethyleneoxy-propyleneoxy glycols of the formula, $CH_3O(CH_2—CH_2O)_a—(CH_2—CH(CH_3)O)_b—CH_2—CH$ $(CH_3)OH$, where a and b are integers ranging from about 10 to about 250. Particularly useful and preferred polyalkyleneoxy compound is MPEG.

As mentioned earlier, by varying the molecular weight of the polyalkyleneoxy compound in the substitution step (step (b), Scheme II), it is possible to alter the HLB value of the resulting organosilane derivatized long-chain compound, Formula V. Typically, the higher the molecular weight of the polyalkyleneoxy compound the higher the HLB number of the resulting organosilane derivative. The organosilane derivatives having an HLB numbers of from about 10 to about 18 are particularly preferred.

The temperature at which the substitution step (b) in Scheme II is conducted ranges from about 0° C. to about 100° C., preferably from about 10° C. to about 50° C. The pressure in this step (b) is not critical and can be sub-atmospheric, atmospheric or super-atmospheric.

In Scheme II, step (c) is a hydrolysis step and corresponds to step (b) of Scheme I and can be carried out under essentially similar conditions in the presence of a suitable base. The resulting organosilanol derivative of a long-chain olefinic compound, Formula VI spontaneously forms a dispersion in aqueous medium. As stated earlier, the dispersion can be solubilized by addition of a suitable solvent to form a clear solution or can be used as a colloidal suspension, microemulsion, emulsion, or a suspension depending on the particulate size of the resulting organosilanol surfactant (Formula VI) as described above.

This invention is further illustrated by the following examples which are provided for illustration purposes and in no way limit the scope of the present invention.

EXAMPLES (GENERAL)

In the Examples that follow, the following abbreviations are used:

HERO —High erucic acid rape seed oil.

HSCR—Hydrosilylated high erucic acid rape seed oil.

HSMETO—Hydrosilylated methyl ester of tung oil (eleostearic acid).

MPEG—Methyl capped polyethylene glycol, $CH_3O$ $(CH_2—CH_2O)_n—CH_2—CH_2—OH$.

$T_g$—Glass transition temperature.

NMR—Nuclear magnetic resonance spectroscopy, usually of either proton, $^1H$; carbon 13, $^{13}C$; and/or silicon 29, $^{29}Si$ nuclei.

IR—Infrared spectroscopy.

DSC—Differential Scanning Calorimetry.

MFT—Minimum film forming temperature.

General Analytical Techniques Used for the Characterization: A variety of analytical techniques were used to characterize the organosilane derivatized long-chain olefinic compounds of this invention which included the following:

NMR: $^1H$ and $^{13}C$ NMR spectra were recorded on a Bruker AX-200 MHz spectrometer with 5 mm probes at 200 and 50 MHz, respectively. $^{29}Si$ NMR spectra were recorded on a Bruker AX-300 MHz spectrometer with 5 and 10 mm probes at a frequency of 60 MHz.

Elemental Analysis: Quantitative estimation of silicon was performed by incinerating a weighed quantity of hydrosilylated material in silica crucibles at 1000° C. for 1 hour and cooling to room temperature.

Iodine value—It is the number of grams of iodine that combine with 100 grams of oil or fat which gives the degree of unsaturation of the acids in the substance. It is typically measured in carbon tetrachloride solution of the substance and treating it with a solution of iodine and mercuric chloride in ethanol.

Hiding Efficiency: The hiding efficiency was measured in accordance with ASTM procedure No. D 2805.

Gloss Measurements were made using a Gardco statistical novogloss meter in accordance with ASTM D 523-89.

Degree of Rusting was measured in accordance with ASTM Specification D610-85 (re-approved 1989), a standard test method used for evaluating degree of rusting on painted steel surfaces.

Cross-Hatch Adhesion tests were made in accordance with ASTM procedure No. D3359-87, a standard test method used for measuring adhesion by tape test.

DSC: A Mettler DSC-30 was used to determine the $T_g$ of the films (mid point value). The heating rate was maintained at 10° C./minute, generally, over a temperature range of −50° C. to 100° C. The flow rate of nitrogen is maintained at 20 mL/min.

MFT: MFT of latexes were determined by a MFFT Bar 90 equipment from Byk-Gardner in accordance with ASTM procedure No. D 2354.

Example 1

To 24.0 grams (0.10 mol of double bond equivalent, estimated from iodine value) of HERO, 50.0 mL of toluene that was freshly distilled from sodium was added and stirred to dissolve the oil. Dichloromethylsilane (4.0 mL, 0.04 mol) was dissolved in 25.0 mL of toluene in a pressure equalizer addition funnel. The oil that was dissolved in toluene was heated to 40° C. (sand bath temperature) and 0.18 grams of platinumdivinyltetramethyldisiloxane catalyst solution was added. To this warm solution of the oil, dichloromethylsilane was added dropwise with stirring under nitrogen over a period of 45 minutes. After complete addition of dichloromethylsilane, the solution had a dark tan color and was heated to reflux and the reaction was continued for 14 hours. Toluene was evaporated using a rotary evaporator after the completion of reaction time. The dark oily residue was dried in vacuo for 72 hours during which time a highly viscous oil with an amorphous solid, a combined weighing of 24.3 grams, had formed. The product, hydrosilylated high erucic acid rape seed oil (HSCR) was stored under nitrogen before use. The structure of the product was verified by $^1H$, $^{13}C$ and $^{29}Si$ NMR and IR spectroscopy. Total amount of hydrosilylation by $^1H$ NMR analysis was found to be 24%.

Example 2

To 2 grams of HSCR obtained in Example 1, an equal amount of water was added and the mixture was stirred vigorously in an aspirator vacuum until all the liberated HCl gas was removed. A stable emulsion was formed with ease without the aid of any surfactant. The emulsion has a pleasant odor and does not settle on standing.

The hydrosilylated product so formed was laid on a Q panel, and was dried overnight in vacuo. It was then heated at 85° C. for two minutes to drive off any residual moisture. The dried product was a rubbery material insoluble in common organic solvents. The structure of the product was verified by $^{29}$Si solid state NMR.

Example 3

Example 1 was substantially repeated in Example 3 with the exception that the reaction was carried out using tung oil instead of HERO as follows. To 75.1 grams of tung oil (0.490 mol of double bond equivalent, estimated from iodine value of tung oil), 150.0 mL of toluene that was freshly distilled from sodium was added and stirred to dissolve the oil. Dichloromethylsilane (7.83 mL, 0.076 mol) was dissolved in 50.0 mL of toluene in a pressure equalizer addition funnel. The oil that was dissolved in toluene was heated to 40° C. (sand bath temperature) and 0.563 grams of platinumdivinyltetramethyldisiloxane catalyst solution was added. To this warm solution of the oil, dichloromethylsilane was added dropwise with stirring under nitrogen over a period of 45 minutes. After complete addition of dichloromethylsilane, the solution had a dark tan color and was heated to reflux and the reaction was continued for a period of additional 5 hours. Toluene was evaporated using a rotary evaporator after the completion of reaction time. The dark oily residue was dried in vacuo for 72 hours during which time a highly viscous oil with an amorphous solid, a combined weighing of 84.2 grams had formed. The product, hydrosilylated tung oil was characterized in a fashion similar to HSCR as given in Example 1.

Example 4

Example 1 was substantially repeated in Example 4 with the exception that the reaction was carried out using linseed oil instead of HERO as follows. To 41.0 grams of linseed oil (0.266 mol of double bond equivalent, estimated from iodine value of linseed oil), 150.0 mL of toluene that was freshly distilled from sodium was added and stirred to dissolve the oil. Dichloromethylsilane (9.70 mL, 0.0887 mol) was dissolved in 50.0 mL of toluene in a pressure equalizer addition funnel. The oil that was dissolved in toluene was heated to 40° C. (sand bath temperature) and 0.500 grams of platinumdivinyltetramethyldisiloxane catalyst solution was added. To this warm solution of the oil, dichloromethylsilane was added dropwise with stirring under nitrogen over a period of 45 minutes. After complete addition of dichloromethylsilane, the solution had a dark tan color and was heated to reflux and the reaction was continued for 5 hours. Toluene was evaporated using a rotary evaporator after the completion of reaction time. The dark oily residue was dried in vacuo for 72 hours during which time a highly viscous oil with an amorphous solid, a combined weighing of 51.7 grams had formed. The product, hydrosilylated linseed oil was characterized in a fashion similar to HSCR as given in Example 1.

Example 5

Example 1 was substantially repeated in Example 5 with the exception that the reaction was carried out using methyl ester of eleostearic acid instead of HERO as follows. The methyl ester of eleostearic acid was obtained by the transesterification of tung oil with methanol using sodium hydroxide as the base. A 5 L kettle was set-up with a dropping funnel, condenser, and a nitrogen inlet. The reactor was first flushed with nitrogen. To this kettle, 172.2 grams of methyl ester of eleostearic acid was added followed by the addition of 0.95 grams of platinumdivinyltetramethyldisiloxane catalyst solution. The reaction mixture was heated to 40° C. Dichloromethylsilane (43.8 mL, 0.381 mol) was added in drops to the reaction mixture over a period of one hour. During the addition, the reaction mixture was stirred vigorously to ensure thorough mixing. After complete addition of dichloromethylsilane, the solution had a dark tan color. At this time the temperature of the reaction was raised to 110° C. and the reaction was continued for another three hours. After the reaction was over, the product was cooled to room temperature. The dark tan product, termed HSMETO, was hydrolyzed as such without further purification.

Example 6

Example 5 was substantially repeated in Example 6 with the exception that the following amounts of starting materials and reagents were employed:

Methyl ester of eleostearic acid 33.9 grams
Dichloromethylsilane 3.9 grams
Platinumdivinyltetramethyldisiloxane solution 0.156 grams The hydrosilylation reaction was carried out at a temperature of about 140°–150 ° C for a period of about 4 hours. The yield of the resulting hydrosilylated product, HSMETO was 35.9 g (95%). This product was used as such in the next step of substitution reaction with MPEG without any further purification.

Example 7

This Example illustrates the substitution reaction of MPEG with HSMETO as formed in Example 6. To 35.9 grams of HSMETO taken in a 1 L Kettle, 180 grams of MPEG of the formula, $CH_3O(CH_2—CH_2)_nCH_2—CH_2—OH$, where n is 45, dissolved in about 180 grams of methylene chloride was added over a period of about 1 hour. The stirring was continued for an additional period of about 8 hours during which time complete substitution of one of the chlorine atoms in HSMETO with MPEG took place. Evaporation of the solvent from reaction mixture resulted in 200 grams of the product in the form of a waxy solid (95% yield).

Example 8

This Example illustrates the hydrolysis of MPEG substituted hydrosilylated product obtained in Example 7. To 220 grams of MPEG substituted HSMETO, 200 mL of 10% ammonium hydroxide solution was added with vigorous stirring over a period of 2 hours. The pH of the solution during this addition was maintained at about 8 by addition of appropriate amounts of ammonium hydroxide solution. A stable emulsion was formed with ease without the aid of any other surfactant. The estimated yield of the emulsion containing, HSMETO-MPEG, was about 380 grams.

Example 9

This Example illustrates the utility of the emulsions formed according to Example 2 of the present invention in the dispersion of a pigment such as carbon black for coating applications. A carbon black of 13 μm particle diameter was chosen for this study, and a concentration of 6% dispersant to pigment by weight was used for the pigment grind composition. The results indicate that the pigment grind formulation containing the HSCR emulsion formed in accordance with Example 2 features much better properties than the control as evidenced by the improved hiding efficiency, gloss, degree of rusting for panels, and cross-hatch adhesion properties. The following table shows the composition of the pigment grind formulation and control used (Table 1).

TABLE 1

| | Amounts in grams | |
|---|---|---|
| Reagents | Example 9 | Control |
| Carbon Black[a] (pigment) | 16.0 | 16.0 |
| Deionized water | 160.0 | 160.0 |
| HSCR (dispersant from Example 1) | 0.96 | 0.0 |
| Commercial Dispersant (CD) | 0.0 | 0.96 |
| Byk 022[b] (defoamer) | 0.0 | 0.2 |

[a]obtained from Cabot;
[b]obtained from Byk Chemie.

The materials given in Table 1 were premixed using a Lightnin mixer at 300 rpm for 15 minutes. The dispersion process was continued with transfer to an Eiger "mini" 250 bead mill grinder with a 50% bead charge and was dispersed at 3000 rpm for 20 minutes to a Hegmann grid of 8. The pigment grind composition so formed was then used in a white latex paint of the composition given in Table 2.

TABLE 2

| Reagents | Amount in grams | Supplier |
|---|---|---|
| TiO2 | 590.0 | Dupont |
| Deionized Water | 310.0 | — |
| Tamol 681 | 14.0 | Rohm and Haas |
| Bubble Breaker 2056a | 4.2 | Witco |
| Let Down | | |
| Aquamac 700 | 916.0 | McWhorter |
| Texanol | 7.0 | Exxon |
| RM 825 | 4.2 | Rohm and Haas |

For evaluation of the pigment grind compositions given in Table 1, four different levels of latex formulations were made with the white latex paint formed from the formulation given in Table 2: 5.7%, 10.5%, 15.0% and 20.0%. These compositions were made by mixing specified grams of pigment grinds with 100 grams of the white latex paint, i.e., 5.7% HSCR means 5.7 grams of pigment grind formulation from Table 1 mixed with 100 grams of white latex formulation of Table 2 and so on. The performance properties of these formulations are given in Table 3.

TABLE 3

| Performance Properties | | | | | | |
|---|---|---|---|---|---|---|
| Hiding Efficiency at Pigmented Mill Base Concentration | | Example 9 | | | Control | |
| 5.7% | | 99.3 | | | 98.1 | |
| 10.5% | | 99.7 | | | 98.5 | |
| 15.0% | | 99.8 | | | 98.9 | |
| 20.0% | | 100.0 | | | 100.0 | |
| Gloss Measurements at Pigmented Mill Base Concentration | 20° | 60° | 85° | 20° | 60° | 85° |
| 5.7% | 11.5 | 54.7 | 78.7 | 8.6 | 54.1 | 78.5 |
| 10.5% | 6.3 | 47.9 | 77.1 | 5.2 | 41.0 | 68.7 |
| 15.0% | 3.7 | 33.1 | 37.0 | 2.8 | 29.9 | 32.0 |
| 20.0% | 0.7 | 8.4 | 57.1 | 0.6 | 7.7 | 50.5 |
| Degree of Rusting for Panels Coated with Carbon Black Paint Formulated at Pigmented Mill Base Concentration. | Film Thickness | Area in % Rusting | Rusting Grade[a] | Film Thickness | Area in % Rusting | Rusting Grade[a] |
| 5.7% | 2.02 | 0.03 | 10 | 2.06 | 0.3 | 7 |
| 10.5% | 1.7 | 0.03 | 9 | 1.67 | 10.0 | 4 |
| 15.0% | 1.84 | 0.3 | 7 | 1.77 | 16.0 | 3 |
| 20.0% | 1.96 | 10.0 | 4 | 1.82 | 50.0 | 1 |
| Cross-Hatch Adhesion at Pigmented Mill Base Concentration. | Dry Film Thickness | Adhesion Classification[b] | | Dry Film Thickness | Adhesion Classification[b] | |
| 5.7% | 1.2 | 5B | | 1.4 | 4B | |
| 10.5% | 1.4 | 5B | | 1.48 | 3B | |
| 15.0% | 1.32 | 5B | | 1.35 | 3B | |
| 20.0% | 1.33 | 4B | | 1.2 | 2B | |

[a]10 = best, 0 = worst;
[b]5B = best, 0B = worst

Example 10

This Example illustrates the dispersion of phthalocyanine green (obtained by the chlorination of phthalocyanine blue) in a stable emulsion formed in accordance with Example 2 using HSCR. Phthalocyanine green with a particle size distribution of 0.03–0.12 µm and with a surface area of 77 meters/square gram was used. The dispersion procedure as outlined in Example 9 was used. The pigment grind compositions for HSCR and control are given in Table 4.

TABLE 4

| | Amounts in grams | |
|---|---|---|
| Reagents | Example 10 | Control |
| Phthalocyanine Green[a] (pigment) | 16.0 | 16.0 |
| Deionized water | 160.0 | 160.0 |
| HSCR (dispersant from Example 1) | 0.96 | 0.0 |
| Commercial Dispersant (CD) | 0.0 | 0.96 |
| Byk 022[b] (defoamer) | 0.0 | 0.2 |

[a]Obtained from Sun Chemical;
[b]obtained from Byk Chemie.

The pigment grinds so formed were again mixed with a white latex formulation as given in Table 2 of Example 9. The following four paint grind compositions of Example 10 and the control were made: 5%, 11%, 15%, and 20% following the procedures of Example 9. The performance properties, hiding efficiency, and gloss, are summarized in Table 5.

TABLE 5

Performance Properties

| Hiding Efficiency at Pigmented Mill Base Concentration. | Example 10 | Control |
|---|---|---|
| 5.0% | 99.0 | 98.2 |
| 11.0% | 99.5 | 98.4 |
| 15.0% | 99.9 | 99.1 |
| 20.0% | 100.0 | 99.2 |

| Gloss Measurements at Pigmented Mill Base Concentration. | 20° | 60° | 85° | 20° | 60° | 85° |
|---|---|---|---|---|---|---|
| 5.0% | 8.77 | 45.2 | 71.5 | 8.41 | 44.5 | 61.3 |
| 11.0% | 7.05 | 43.2 | 72.4 | 4.08 | 33.8 | 67.15 |
| 15.0% | 7.08 | 41.5 | 37.4 | 2.5 | 24.7 | 32.8 |
| 20.0% | 2.11 | 16.4 | 31.2 | 1.61 | 15.54 | 26.1 |

Example 11

This Example illustrates the use of organosilanol derivatized long-chain olefinic ester as a surfactant in emulsion polymerization. A latex containing vinyl acetate (VA) and butyl acrylate (BA) monomers was synthesized as follows. A 500 mL reactor kettle was charged with deionized (DI) water and was deoxygenated for 1 hour at 80° C. This water was cooled to ambient temperature and used as DI and Deoxygenated (DO) water in the initial charge, pre-emulsion mixture and initiator solutions. The initial charge in the reactor included: 100 grams of DI water; 3.12 grams of hydrosilylated methyl ester of eleostearic acid, HSMETO (53% solids) made in accordance with Example 5; 2.63 grams of Rhodofac BX 660 (Rhone Phoulenc Inc. 80% solids); 0.54 grams of sodium carbonate; and 0.06 grams of ammonium persulfate. The reactor was then agitated at 200 rpm using a propeller angled at 45 degrees for 15 minutes to obtain a homogeneous mixture. The catalyst was added just before the addition of monomers.

A monomer mixture was prepared comprising the following monomer ratios: 75 grams of VA; 23.5 grams of BA; 0.75 grams of Sipomer Wam I (adhesion promoter from Rhone Poulenc Inc.); and 0.75 grams of Sipomer Wam II (adhesion promoter from Rhone Poulenc Inc.). The initiator solution was prepared by dissolving 0.4 grams of ammonium persulfate in 20.0 grams of DI water.

The monomer and initiator were fed separately using a peristaltic and syringe pump and using an automated data acquisition and control program. First, about 2 grams of the monomer mixture was added quickly into the reaction flask. The impeller was rotated at 200 rpm and the temperature was maintained at 80° C. using a water bath. A 10 minute reaction time was allowed for preseeding of the monomer initially added. After this time, the monomer addition was continued at a rate of 0.8 grams per minute for 1 hour and 50 minutes. To maintain starve fed conditions, the initiator solution was added for 2 hours and 9 minutes at a rate of 9.42 mL per hour.

After the addition of monomer mixture, the reactants were allowed to react for another 2 hours at 80° C. After which it was cooled slowly to ambient temperature. During this time, chaser solutions containing 0.03 g of t-butyl hydroperoxide in 4 mL of water and 0.04 grams of sodium formaldehyde sulfoxylate in 4 mL of water were added separately via syringe pumps. After reaction completion, the latex was filtered through a cheese cloth and was ready for property evaluation. The latex physical properties are given in the table below.

TABLE 6

| Properties | VA/BA/WamI/WamII |
|---|---|
| % Solids | 44.4 |
| % Conversion | 99.0 |
| % Coagulated | none |
| % Solid isolated on the sides of the reactor and impeller | 1.0 |
| pH (as such after polymerization) | 4.85 |
| MFT, °C. | −1.5 |
| $T_g$, °C. of dried film* (Experimental) | 37.1 (Final $T_g$ of the latex after 6 months) |
| $T_g$, °C. (Theoretical by Fox equation) | 7.0 |
| Particle size (nm) | 166 |
| Nature of film | clear |
| Latex drying time | 2 h |

*Latex film cast after adding 0.1% by weight cobalt hydrocure II and 0.1% Dri-RX-HF based on latex solids Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. An organosilane derivatized compound comprising a long chain olefinic compound of the formula:

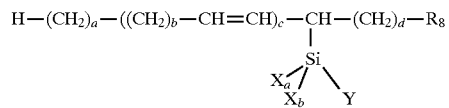

wherein
(a) $R_8$ is selected from the group consisting of —COOR', —CN, —CONR"R'", and —CH$_2$NR"R'", where R', R", R'" are the same or different and are independently selected from the group consisting of phenyl, tolyl, benzyl, a linear or branched alkenyl group having 2 to 10 carbon atoms, a linear or branched alkyl and fluoroalkyl groups having the formula $C_nH_xF_y$, where n is an integer from 1 to 10, x and y are integers from 0 to 2n+1. and the sum of x and y is 2n+1, and R' can also be a multifunctional moiety having the structure:

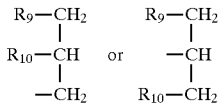

where $R_9$ and $R_{10}$ are the same or different, and are independently selected from the group consisting of a saturated or unsaturated fatty acid chain, acrylic, and a linear or branched alkyl and alkenyl carboxylic acid moiety having 2 to 20 carbon atoms;

(b) $X_a$ is hydroxy and $X_b$ is either polyethyleneoxy group of the formula $CH_3O(CH_2—CH_2O)_n—CH_2—CH_2O—$, or polypropyleneoxy group of the formula $CH_3O(CH_2—CH(CH_3)O)_n—CH_2—CH(CH_3)O$, where n is an integer ranging from 10 to 250;

(c) Y is an aliphatic or an aromatic moiety having 1 to 20 carbon atoms; and (d) a, b, c, and d are integers, where a ranges from 0 to 20, b ranges from 0 to 4, c ranges from 1 to 4, and d ranges from 0 to 20.

2. The compound as set forth in claim 1 wherein $R_8$ is —COOR'.

3. The compound as set forth in claim 2 wherein it is derived from a fatty acid selected from the group consisting of eleostearic acid, linoleic acid, linolenic acid, and arachidonic acid.

4. The compound as set forth in claim 3 wherein Y is an alkyl group having 1 to 4 carbon atoms.

5. An organosilanol compound comprising a long chain olefinic ester of the formula:

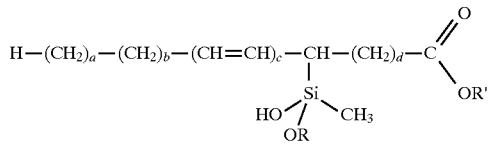

wherein (a) R' is either methyl group or a group derived from a fatty oil selected from the group consisting of tung oil, high erucic rape seed oil, and linseed oil;

(b) —OR is either polyethyleneoxy group of the formula $CH_3O(CH_2—CH_2O)_n—CH_2—CH_2O—$, or polypropyleneoxy group of the formula $CH_3O(CH_2—CH(CH_3)O)_n—CH_2—CH(CH_3)O$, where n is an integer ranging from 25 to 100; and (c) a, b, c, and d are integers, where a ranges from 4 to 7, b ranges from 0 to 3, c ranges from 1 to 3, and d ranges from 5 to 13.

6. The compound as set forth in claim 5 wherein —OR is a polyethylencoxy group of the formula $CH_3O(CH_2—CH_2O)_n—$, where n is an integer ranging from 25 to 100.

7. The compound as set forth in claim 5 wherein said compound exhibits a hydrophilic/lipophilic balance (HLB) number in the range of from about 12 to about 16.

8. A composition comprising an organosilanol derivatized long chain olefinic ester of claim 5 and a material selected from the group consisting of pigments and anti-corrosive additives wherein said long chain olefinic ester is suitable for dispersing said material.

* * * * *